United States Patent
Runkel

(10) Patent No.: US 6,576,223 B2
(45) Date of Patent: *Jun. 10, 2003

(54) INSECT REPELLENT

(75) Inventor: Frank Runkel, Buseck (DE)

(73) Assignee: Karl Engelhard Fabrik Pharm Praparate GmbH & Co. KG. (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/451,016

(22) Filed: Nov. 29, 1999

(65) Prior Publication Data

US 2002/0054909 A1 May 9, 2002

Related U.S. Application Data

(63) Continuation of application No. PCT/EP98/03008, filed on May 22, 1998.

(30) Foreign Application Priority Data

May 27, 1997 (DE) .......................................... 197 22 196

(51) Int. Cl.[7] .............................................. A01N 25/06

(52) U.S. Cl. .................. 424/45; 424/405; 424/DIG. 11; 514/617; 514/919

(58) Field of Search ................................ 514/919, 617; 424/484, 405, 485, 59, 45, 47, 61, 63, DIG. 10

(56) References Cited

FOREIGN PATENT DOCUMENTS

| CH | A-9506460 | 4/1997 |
|----|-----------|--------|
| DE | 32 11 632 A1 | 3/1982 |
| DE | 3206346 | * 9/1983 |
| DE | 3211 633 | 10/1983 |
| DE | 197 22 196 C1 | 5/1997 |
| EP | 0090 288 | 10/1983 |
| EP | 0 251 464 | 1/1988 |
| EP | 98/03008 | 5/1998 |
| GB | 1 575 387 | 5/1978 |
| JP | 830098489 | 6/1983 |
| JP | 860054899 | 3/1986 |
| JP | 910089390 | 3/1991 |
| JP | 910355232 | 12/1991 |
| JP | 880181754 | 5/1992 |
| JP | 920148242 | 5/1992 |
| RU | 950103614 | 3/1995 |
| SU | 442960 | 5/1982 |
| WO | WO 95/07024 | 3/1995 |
| WO | WO 97/49380 | 12/1997 |

OTHER PUBLICATIONS

XP–002077855 Derwent Abstract 98–82905 Qiu et al Formulation —Pharm. Res. 14 #11 Supp. S–313, 1997.*

* cited by examiner

Primary Examiner—Neil S. Levy
(74) Attorney, Agent, or Firm—St. Onge Steward Johnston & Reens LLC

(57) ABSTRACT

An insect-repelling agent contains N,N-diethyl-m-toluamide (DEET) based on alcohol solutions as the active ingredient (repellent), and further contains an adjuvant that extends the period of effectiveness of DEET following application to human skin. It is proposed that the sole adjuvant is glycerol in an amount of more than 10 percent by weight of the insect-repelling.

7 Claims, 2 Drawing Sheets

INSECT REPELLENT

CROSSREFERENCE OF PENDING APPLICATION

This application is a continuation of international application PCT/EP98/03008 filed May 22, 1998, and claims priority benefit based on DE Application No. 19722196.3, filed May 27, 1997.

BACKGROUND OF THE INVENTION

The present invention relates to an insect-repelling agent containing N,N-diethyl-m-toluamide (DEET) based on alcohol solutions as the active ingredient (repellent), and an adjuvant that extends the period of effectiveness of DEET following application to human skin.

An insect-repelling agent of this kind is known from EP 0 090 288 B1.

DEET (N,N-diethyl-m-toluamide) is a known and proven insect-repelling agent (called a "repellent").

In known insect-repelling agents, DEET is present as an alcohol solution. When an alcohol solution of this kind is applied to the skin, the period of effectiveness is about 5 hours.

For a desirably long effectiveness in the range from 6 to 8 hours following application to human skin, adjuvants that extend the period of effectiveness have been discovered.

In the context of EP 0 090 288 cited above, it was found that by adding the adjuvant polyethylene glycol 400 (PEG-400), it was possible to achieve greatly reduced resorption and an improved period of effectiveness of the actual active ingredient, i.e. the DEET repellent. The polyethylene glycol 400 adjuvant itself possesses no repellent effect. By adding the PEG-400 adjuvant to alcohol solutions of DEET, it was possible to increase the period of effectiveness. For example, the period of effectiveness of 20% DEET in isopropanol was increased from 5.7 to 7.4 hours by adding 20% PEG-400. EP 0 090 288 has also disclosed the use of univalent or polyvalent alcohols, e.g. including glycerol, as solvents. One exemplary embodiment describes a formulation made up of 15 parts DEET as active ingredient (repellent), 13 parts PEG-400 as adjuvant to extend the period of effectiveness, and a mixture of 10 parts glycerol, 8 parts water, and 53 parts isopropanol as solvent.

It has now been found, in the practical use of such insect-repelling agents, that a period of effectiveness in the range of 7 to 8 hours is not sufficient to achieve an effect that lasts an entire day.

In the summer months in particular, in which insects are a problem, the days are substantially more than 8 hours long, i.e. the period during which a person is exposed to insects in the course of a day is substantially longer than 8 hours. The result is that an insect-repelling effect cannot be achieved for an entire day with one application per day, for example in the morning, of such an insect-repelling agent.

The use of higher concentrations of DEET or the use of higher concentrations of the PEG-400 adjuvant that extends the period of effectiveness either did not produce any substantial improvement, or the disadvantages associated therewith rule out such increases.

According to the monograph "Diethyltoluamid" [Diethyltoluamide] (Bundesanzeiger No. 137, Jul. 23, 1994), blistering, ulceration, and necroses can occur as side effects at concentrations of DEET exceeding 30%.

Contact allergies can occasionally occur with polyethylene glycols, especially with the liquid polyethylene glycols PEG-200 to -400 (A. Zesch, Externa, Springer Verlag 1980).

In addition, polyethylene glycols exhibit the following undesirable reactions, i.e. they form peroxides when exposed to oxygen or air; react with substances that contain phenolic OH-groups, such as cresols, tannins, resorcin, or salicylic acid; and exhibit discoloration with sulfonamides, anthrasol, chrysarobin, or theophylline.

PEG's moreover cause inactivation of certain antibiotics and preservatives, for example penicillins and p-hydroxybenzoates. PEG's also cause dissolution of plastics such as polyethylene, PVC, and cellulose esters (Sucker et al., Pharm. Technologie, 2nd ed. 1991).

These reactions with PEG's result in a chemical change that can impair the effectiveness and shelf life of the insect-repelling agent, cause visible discoloration of skin areas to which the insect-repelling agent is applied, and possibly adversely affect other agents applied to or contained in the skin, for example antibiotics or preservatives.

It is common practice in the summer months to use sunscreens that contain, for example, preservatives. If the PEG then reacts with a preservative of a sunscreen, the latter exhibits decomposition phenomena that result not only in loss of effectiveness but often also in an unpleasant odor. If the repellent is applied to a skin area that has been coated with antibiotics because of an injury, adverse effects (inactivation) can occur.

Against this background, it is the object of the present invention to equip an insect-repelling agent of the kind cited initially with an adjuvant that on the one hand considerably extends the period of effectiveness of DEET, and on the other hand is tolerated by human skin without interactions and also does not participate in any undesirable reactions.

SUMMARY OF THE INVENTION

According to the present invention, the object is achieved in that the sole adjuvant for extending the period of effectiveness is glycerol in an amount of more than 10 percent by weight of the insect-repelling agent.

Intensive investigations have revealed, surprisingly, that glycerol is usable as an adjuvant that effectively extends the period of effectiveness of DEET.

It is possible to replace the PEG-400 adjuvant with glycerol, so that glycerol can be used as the only and exclusive adjuvant extending the period of effectiveness of DEET.

This effect may be regarded as surprising especially because, despite the known use of glycerol as a solvent, efforts have been made in the existing art to find other adjuvants that extend the period of effectiveness of DEET, leading to the PEG-400 adjuvant in the case of the aforementioned EP 0 090 288. It is therefore to be considered surprising that glycerol can be used as the only and thus exclusive adjuvant for extending the period of effectiveness of alcohol-based DEET formulations.

Glycerol is a natural substance that occurs in human metabolism. In dermatology, glycerol is used as an additive for the care of irritated, brittle dry skin. Glycerol causes absolutely no contact allergies even in highly sensitive allergic persons, so that it can be used even by such sensitive persons. It is to be expected that insect-repelling agents of this kind will be used mostly during the vacation season, in which users are in an unfamiliar environment and extensively exposed to mosquitoes as well as usually to higher temperatures with intensive solar radiation. Persons with sensitive skin then react to additional agents applied to the skin, for example an insect-repelling agent, with allergic reactions.

Intensive investigations have shown that when glycerol is the adjuvant of an insect-repelling agent, such reactions do not occur. The reactions mentioned earlier—namely peroxide formation when exposed to oxygen and air, reactions with substances that contain phenolic OH groups, discoloration with sulfonamides, and inactivation of antibiotics or preservatives—also do not occur when glycerol is the adjuvant.

The result is not only to make available a highly skin-compatible adjuvant, but also to create the possibility of using it at relatively high concentrations, which results in a further increase in the period of effectiveness without triggering undesirable side effects due to the increased concentration.

It is to be regarded as an even more surprising effect of the replacement of PEG-400 with glycerol that, given comparable quantities of effective ingredient (DEET) and comparable quantities of adjuvant, the period of effectiveness of an insect-repelling agent can be increased to as much as 13 hours with the glycerol adjuvant. The result is thus an increase of 7 hours over the usual period of effectiveness without adjuvants, and of a further 5 hours as compared to the PEG-400 adjuvant.

The overall result is to yield a substantial increase in the period of effectiveness while at the same time reducing or preventing the occurrence of side effects, in particular allergic reactions and reactions with environmental substances or with natural substances contained in the skin or other substances applied to it.

The proportion of glycerol can be up to 60 wt %; it is preferably 20 to 50 wt %.

An optimum extension of the period of effectiveness is achieved in this preferred range: the period of effectiveness is up to 13 hours, i.e. a continuous insect-repelling effect can be obtained, even over a very long and sunny summer day, with a single application in the morning.

In a further embodiment of the invention, the proportion of DEET is 15 to 25 wt %.

The advantage of this feature is that it is possible to work with a quantity of active ingredient (repellent) that on the one hand is sufficient to produce optimum effectiveness over the long term, but at the same time represents a sufficiently small quantity that side effects described in the monograph—such as blistering, ulceration, and necroses—are ruled out.

In a further embodiment of the invention, further repellents are contained in the insect-repelling agent.

This feature, known per se, has the advantage that in particular cases in which the effectiveness of DEET must be assisted because of local or other conditions, further repellents can be utilized.

In a further embodiment of the invention, additives selected from the group comprising perfume oils, fragrances, skin-care substances, water, emulsifiers, and propellants are present.

The advantage of this feature is that by way of the additives it is possible to make available formulations that are pleasant to the skin, or particular galenical presentations can be offered, for example skin sprays, lotions, cremes, or sticks.

The use according to the present invention of glycerol as the adjuvant that extends the period of effectiveness in an insect-repelling agent thus results in an extension of the period of effectiveness with relatively small quantities of actual active ingredient (repellent), thus creating an effective and at the same time tolerable insect-repelling agent.

It is understood that the features mentioned above and those yet to be explained below can be used not only in the combinations indicated, but also in other combinations or in isolation, without leaving the context of the present invention.

BRIEF DESCRIPTION OF THE FIGURES

The invention will be described and explained in more detail below with reference to several selected exemplary embodiments in conjunction with the appended drawings, in which.

DETAILED DESCRIPTION OF PREFERRED EMBODIMENTS

Test Method

Figure 1:
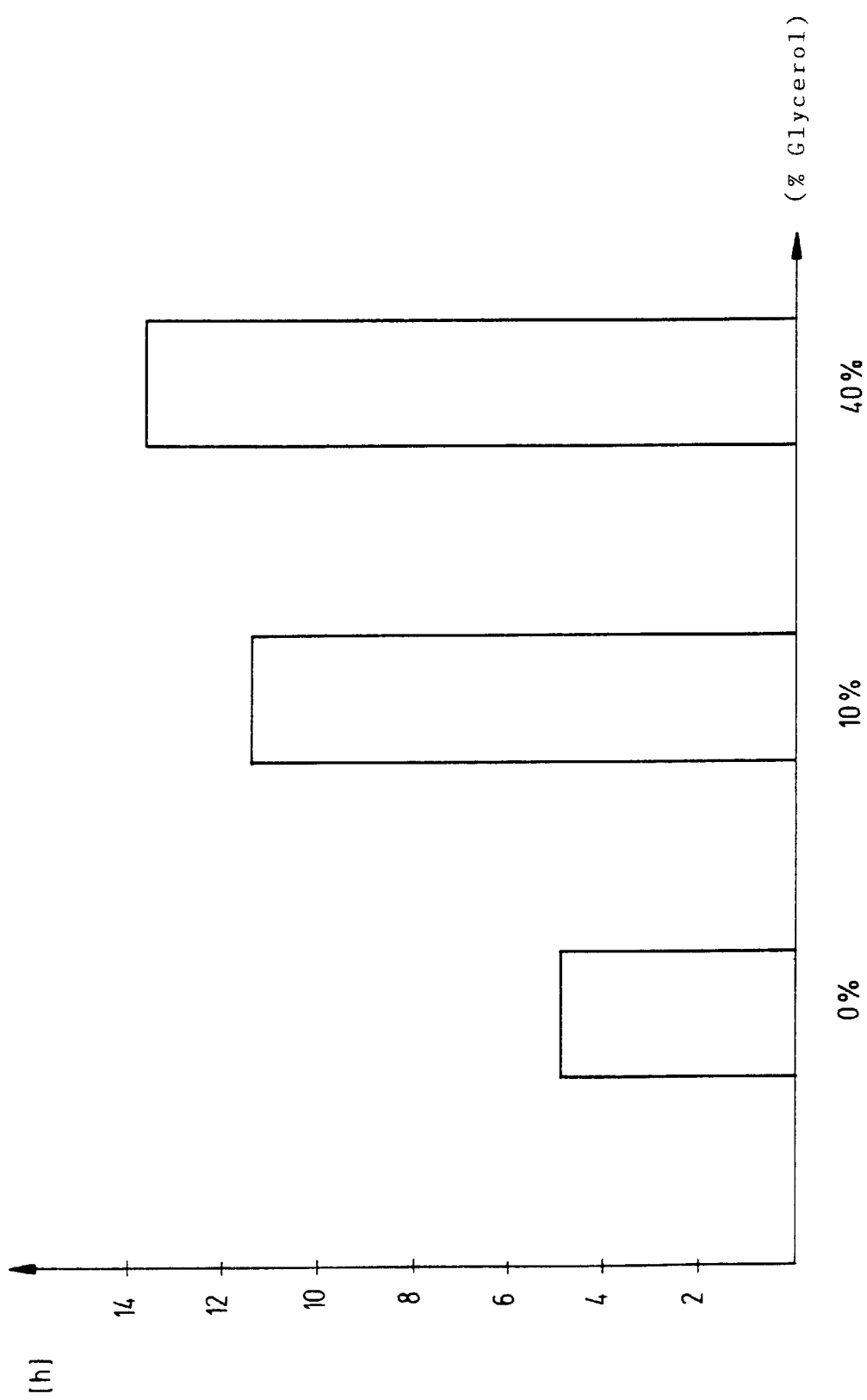
FIG. 1 shows a comparative representation, in the form of a bar chart, of the period of effectiveness of a 20% DEET formulation as a function of glycerol concentration.

The period of effectiveness of the formulations described hereinafter was tested using a proven test method of the Swiss Tropical Institute. The experimental animals used were approximately 300 to 400 exclusively female laboratory-strain yellow-fever mosquitoes (*Aedes aegypti*). The tests were performed in a breeding cage 40×40×40 cm. To ensure that all the female mosquitoes were hungry during the testing phase, their sugar water was withheld the evening before the test day. Each test began between 8:00 and 10:00 a.m.

An area approximately 250 $cm^2$ on the forearm of an experimental subject was treated with the sample being investigated, by uniformly distributing a 2 ml quantity of the corresponding sample. The treated forearm surface was sealed at both ends with mosquito-proof adhesive tape and a short plastic tube. The untreated hand was covered with thick gloves and served simultaneously as a control for the mosquitoes' biting activity.

Care was also taken to ensure that the surfaces treated with the sample remained untouched during the testing period.

For the actual test, the forearm and thus the skin was placed into the mosquito cage every hour, and for a test period of 10 minutes a count was made of the number of mosquitoes that a) attempted to bite through the glove (positive control);

b) flew closer than 3 cm to from the treated surface (at the beginning, middle, and end of the test);

c) remained on the treated surface for longer than 2 seconds; and d) pierced the treated surface and sucked blood.

Analysis and Interpretation

The effectiveness of a sample was determined principally from the ratio between the number of ready-to-feed mosquitoes that landed on the glove, and the other values.

The number of mosquitoes that landed was important because mosquitoes which fly around in the vicinity of a person, or in fact land, also represent a certain irritation.

The number of biting mosquitoes is the decisive factor for the period of effectiveness and thus, in the tropics, for the risk of infection.

Formulations

Formulation without Glycerol

Comparative

A 100-ml quantity contained the following ingredients:

|  | Sample amount (g) |  |
| --- | --- | --- |
| N,N-diethyl-m-toluamide (USP XXII) | 19.000 | (repellent) |
| Ethanol 96% (DAB 10) | 38.000 | (solvent) |
| Isopropyl myristate (EP) | 28.230 | (additive) |
| Bianca perfume oil | 0.240 | (additive) |
|  | 85.470 |  |
| Specific gravity: 0.8547 g/ml |  |  |

Isopropyl myristate represents an additive which ensures that application of the insect-repelling agent produces a pleasant sensation on the skin.

Formulation with 10% Glycerol

A 100-ml quantity contained the following ingredients:

|  | Sample amount (g) |  |
| --- | --- | --- |
| N,N-diethyl-m-toluamide (USP XXII) | 19.000 | (repellent) |
| Ethanol 96% (DAB 10) | 38.000 | (solvent) |
| Glycerol 85% (EP) (vegetable-derived) | 11.000 | (adjuvant) |
| Isopropyl myristate (EP) | 21.100 | (additive) |
| Bianca perfume oil | 0.240 | (additive) |
|  | 89.340 |  |
| Specific gravity: 0.8934 g/ml |  |  |

Formulation with 40% Glycerol

A 100-ml quantity contained the following ingredients:

|  | Sample amount (g) |  |
| --- | --- | --- |
| N,N-diethyl-m-toluamide (USP XXII) | 19.000 | (repellent) |
| Ethanol 96% (DAB 10) | 38.000 | (solvent) |
| Glycerol 85% (EP) (vegetable-derived) | 41.640 | (adjuvant) |
| Bianca perfume oil | 0.240 | (additive) |
|  | 98.880 |  |
| Specific gravity: 0.9888 g/ml |  |  |

The three aforesaid formulations were applied to the skin as described above, and the test already described was performed. The period of effectiveness was assumed to have ended when at least two mosquitoes bit and sucked blood in the treated area during a test period.

FIG. 1 shows the test results for the three formulations, i.e. the formulation without glycerol, formulation with 10% glycerol, and formulation with 40% glycerol. The period of effectiveness (in hours) is plotted on the ordinate.

It is evident from this that even with a concentration of only about 10% glycerol, the period of effectiveness is increased to 11 hours as compared to a formulation without glycerol (5 hours). With a formulation containing 40% glycerol it was possible to increase the period of effectiveness to 13 hours.

In a further test series, an insect-repelling agent with the PEG-400 adjuvant was compared to a formulation according to the present invention with the glycerol adjuvant.

The formulation according to the existing art is available in Germany under the trademark-protected designation AUTAN, and contains 20 g DEET as active ingredient. The PEG-400 concentration is between 20 and 40%.

This known insect-repelling agent was compared to a formulation according to the present invention having 20% DEET as active ingredient (repellent) and 35% glycerol as adjuvant.

The test mentioned earlier was performed with both formulations.

Figure 2:
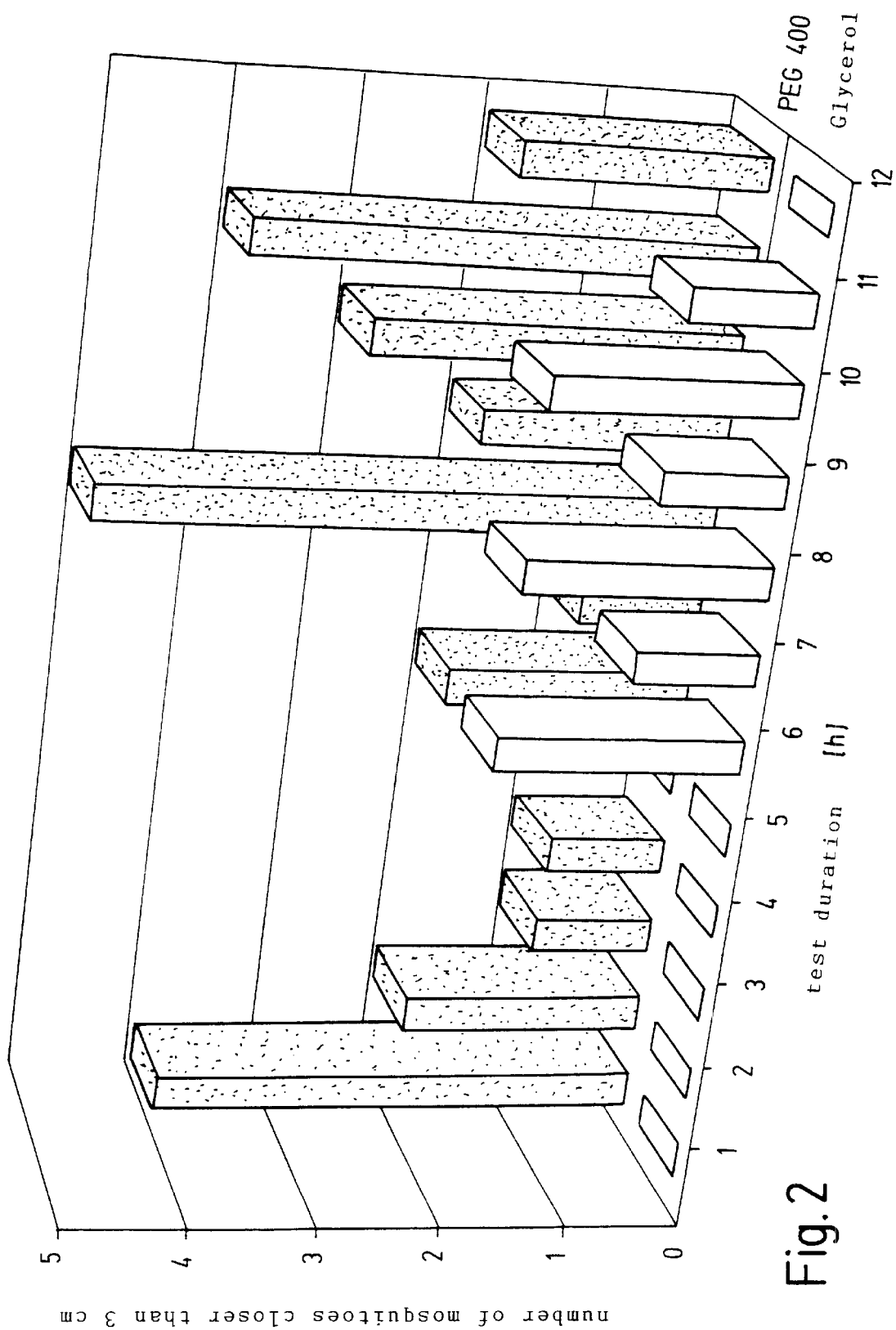
FIG. 2 shows a comparative representation in the form of a perspective bar chart, of the repelling effect of insect-repelling agents having PEG-400 and glycerol.

FIG. 2 shows the repellent effect of the two insect-repelling agents that were compared, indicated as the number of mosquitoes that flew closer than 3 cm to the treated area as a function of test duration.

It is apparent from this that an appreciable repellent effect can be obtained with the glycerol formulation not only in the first hours of the test period, but also 8 to 12 hours after application, thus demonstrating the long-term effectiveness in particularly impressive fashion.

What is claimed is:

1. An insect repellant composition for topical application to human skin comprising:
    a mixture of ethanol and N,N-diethyl-m-toluamide, wherein said N,N-diethyl-m-toluamide is an active ingredient for repelling insects, and glycerol is the sole adjuvant extending the duration of effectiveness of N,N-diethyl-m-toluamide for repelling insects, wherein the content of glycerol is at least 20 percent by weight of said insect repellant composition, wherein the content of N,N-diethyl-m-toluamide ranges of from about 15 to 25 percent by weight of the total weight of the insect repellent composition, and wherein said content of ethanol is at least 37 percent by weight of the total weight of the insect repellent composition.

2. The composition of claim 1 wherein said content of glycerol is up to 60 percent by weight of the total weight of the insect repellent composition.

3. The composition of claim 1 herein said content of glycerol ranges from 20 to 50 percent by weight of the total weight of the insect repellent composition.

4. The composition of claim 1 further comprising at least one additional insect repellant.

5. The composition of claim 1 further comprising an additive for forming stable formulations applicable to the skin selected from the group consisting of perfume, oils, fragrances, propellants, and combinations thereof.

6. The composition of claim 1 further comprising an additive for forming stable formulations applicable to the skin selected from the group consisting of skin-care substances, water, emulsifiers, and combinations thereof.

7. A method of topical application of an insect repellant to human skin comprising the steps of:
    applying a composition containing an insect-repelling agent comprising a mixture of ethanol and N,N-diethyl-m-toluamide, a single adjuvant to extend the duration of effectiveness of N,N-diethyl-m-toluamide as the active ingredient for repelling insects following topical application to human skin, wherein glycerol is the sole adjuvant extending said duration of effectiveness of N,N-diethyl-m-toluamide for repelling insects, wherein the content of glycerol is at least 20 percent by weight of the total weight of said insect repelling composition, wherein the content of N,N-diethyl-m-toluamide ranges of from about 15 to 25 percent by weight of the total weight of the insect repellent composition, and wherein said content of ethanol is at least 37 percent by weight of the total weight of the insect repellent composition.

* * * * *

UNITED STATES PATENT AND TRADEMARK OFFICE
CERTIFICATE OF CORRECTION

PATENT NO. : 6,576,223 B2
DATED : June 10, 2003
INVENTOR(S) : Frank Runkel

It is certified that error appears in the above-identified patent and that said Letters Patent is hereby corrected as shown below:

<u>Title page,</u>
Item [73], Assignee, should read: -- [73] Engelhard Arzneimittel GmbH & Co. KG (DE) --

Signed and Sealed this

Twenty-eighth Day of October, 2003

JAMES E. ROGAN
*Director of the United States Patent and Trademark Office*